US009297793B2

(12) United States Patent
Ueno et al.

(10) Patent No.: US 9,297,793 B2
(45) Date of Patent: Mar. 29, 2016

(54) FUEL PROPERTY SENSOR AND METHOD FOR DETECTING MALFUNCTION OF THE SAME

(71) Applicant: DENSO CORPORATION, Kariya, Aichi-pref. (JP)

(72) Inventors: Masato Ueno, Takahama (JP); Jun Tarui, Kariya (JP)

(73) Assignee: DENSO CORPORATION, Kariya (JP)

( * ) Notice: Subject to any disclaimer, the term of this patent is extended or adjusted under 35 U.S.C. 154(b) by 148 days.

(21) Appl. No.: 14/186,660

(22) Filed: Feb. 21, 2014

(65) Prior Publication Data

US 2014/0312921 A1  Oct. 23, 2014

(30) Foreign Application Priority Data

Apr. 23, 2013 (JP) ................................. 2013-90243

(51) Int. Cl.
 *G01R 27/26* (2006.01)
 *G01N 33/28* (2006.01)
 *G01N 27/22* (2006.01)
 *G01R 17/16* (2006.01)

(52) U.S. Cl.
 CPC .......... *G01N 33/2852* (2013.01); *G01N 27/221* (2013.01); *G01N 27/226* (2013.01); *G01N 27/228* (2013.01); *G01R 27/2605* (2013.01); *G01R 17/16* (2013.01); *G01R 27/26* (2013.01)

(58) Field of Classification Search
 CPC .............. G01N 27/221; G01N 27/226; G01N 33/2852; G01N 2035/1025; G01R 27/2605; G01R 27/26; G01R 17/16
 USPC ........... 324/76.11–76.83, 459–470, 600, 649, 324/500, 503, 509, 512, 519, 658–690; 702/47, 52
 See application file for complete search history.

(56) References Cited

U.S. PATENT DOCUMENTS

| 2003/0033858 | A1* | 2/2003 | Lambert | F02D 41/021 73/53.01 |
| 2005/0253598 | A1* | 11/2005 | Kawahata | G06K 9/0002 324/671 |
| 2006/0049834 | A1* | 3/2006 | Umeda | G01D 5/2405 324/658 |
| 2009/0251126 | A1 | 10/2009 | Ishino et al. | |
| 2010/0244857 | A1* | 9/2010 | Nakamura | G01N 27/226 324/663 |
| 2010/0263647 | A1* | 10/2010 | Uchida | F02D 19/0602 123/704 |

(Continued)

FOREIGN PATENT DOCUMENTS

JP   H01-163862 U   11/1989
JP   H01-166742 U   11/1989

(Continued)

*Primary Examiner* — Huy Q Phan
*Assistant Examiner* — Raul Rios Russo

(57) ABSTRACT

An electrode unit includes a first electrode and a second electrode, which define a space to flow fuel therethough. A detection circuit is connected to the first electrode to charge and discharge the electrode unit and to detect a capacitance of fuel, which flows through the space. A switch device is equipped to a wiring, which connects the second electrode with the ground, and configured to simulate disconnection between the second electrode and the ground. A malfunction detection unit is configured to detect disconnection of the wiring when a difference between a capacitance, which is detected with the detection circuit when the switch device is turned ON, and a capacitance, which is detected with the detection circuit when the switch device is turned OFF, is smaller than a first threshold.

15 Claims, 8 Drawing Sheets

(56) References Cited

U.S. PATENT DOCUMENTS

| | | |
|---|---|---|
| 2010/0264937 A1 | 10/2010 | Tarui et al. |
| 2011/0163761 A1 | 7/2011 | Yokoi et al. |
| 2011/0204877 A1 | 8/2011 | Eguchi |
| 2011/0283773 A1 | 11/2011 | Suzuki |
| 2012/0007828 A1* | 1/2012 | Mizuhashi ............ G06F 3/0412 345/174 |
| 2012/0103059 A1 | 5/2012 | Kimata et al. |
| 2012/0181174 A1* | 7/2012 | Ueno .................... G01N 27/08 204/409 |
| 2012/0299602 A1* | 11/2012 | Chiu ................... G01R 31/026 324/548 |
| 2013/0033275 A1* | 2/2013 | Nakamura ........... G01N 27/226 324/663 |
| 2013/0245869 A1* | 9/2013 | Nishida ................ B60L 3/0069 701/22 |
| 2013/0268209 A1 | 10/2013 | Tashima et al. |

FOREIGN PATENT DOCUMENTS

| | | |
|---|---|---|
| JP | H08-075575 A | 3/1996 |
| JP | 2009-265079 A | 11/2009 |
| JP | 2010-249669 A | 11/2010 |
| JP | 2010-256038 A | 11/2010 |
| JP | 2011-247650 A | 12/2011 |
| JP | 2012-093289 A | 5/2012 |
| WO | 2012-090316 A1 | 7/2012 |

* cited by examiner

FUEL PROPERTY SENSOR AND METHOD FOR DETECTING MALFUNCTION OF THE SAME

CROSS REFERENCE TO RELATED APPLICATION

This application is based on reference Japanese Patent Application No. 2013-90243 filed on Apr. 23, 2013, the disclosure of which is incorporated herein by reference.

TECHNICAL FIELD

The present disclosure relates to a fuel property sensor. The present disclosure relates to a method for detecting malfunction of the fuel property sensor.

BACKGROUND

A known fuel sensor is configured to detect a property of fuel such as a concentration of ethanol contained in fuel for an internal combustion engine of a vehicle. An electronic control unit (ECU) for an engine controls a quantity of fuel injection and a time point of fuel injection according to the property of fuel detected with the fuel sensor. The present configuration enhances drivability of the vehicle and reduces pollution caused by exhaust gas. Patent Document 1 discloses a fuel sensor including an external electrode and a center electrode housed in a housing. The external electrode and the center electrode are immersed in fuel, which flows through the housing, to form a capacitor therebetween. The fuel sensor of Patent Document 1 charges the capacitor with electricity and discharges the charged electricity from the capacitor thereby to detect a capacitance of fuel, which flows between the electrodes. The fuel sensor computes a specific inductive capacity of fuel from the capacitance and detects a concentration of ethanol contained in fuel according to the computed specific inductive capacity.

Patent Document 1

Publication of Japanese Utility Model Application No. H1-163862

In general, a fuel sensor is equipped to a vehicle, and a housing of the fuel sensor is electrically connected with a ground of a battery of the vehicle through a metallic component of, for example, a fueling system of the vehicle. It is assumable that a wiring, which connects the external electrode with the ground, may cause disconnection. In a case of the disconnection, the capacitor, which is formed between the external electrode and the center electrode, and a capacitor, which is unintentionally formed between the external electrode and the housing, may be in parallel connection. Therefore, even in a case of the disconnection, the fuel sensor sends a signal representing a specific capacitance. It is noted that, the fuel sensor disclosed in Patent Document 1 does not include a device to detect disconnection of the wiring, which connects the external electrode with the ground. In the configuration of Patent Document 1, it is assumable that the ECU controls the engine according to the ethanol concentration, which is calculated based on the capacitance detected with the fuel sensor in which the disconnection is caused. Consequently, in this case, drivability of the vehicle may be impaired, and pollution of exhaust gas may be increased.

SUMMARY

It is an object of the present disclosure to produce a fuel property sensor, which is configured to detect disconnection caused between an electrode and a ground. It is another object of the present disclosure to produce a method for detecting malfunction of the fuel property sensor.

According to an aspect of the present disclosure, a fuel property sensor comprises an electrode unit including a first electrode and a second electrode, the first electrode and the second electrode defining a space therebetween, the space configured to flow fuel therethough. The fuel property sensor further comprises a detection circuit connected to the first electrode and configured to charge and discharge the electrode unit to detect a capacitance of fuel, which flows through the space. The fuel property sensor further comprises a switch device equipped to a wiring, which connects the second electrode with the ground, the switch device configured to simulate disconnection between the second electrode and the ground. The fuel property sensor further comprises a malfunction detection unit configured to detect disconnection of the wiring when a difference between a capacitance detected with the detection circuit when the switch device is turned ON and a capacitance detected with the detection circuit when the switch device is turned OFF is smaller than a first threshold.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION

As follows, embodiments of the present disclosure will be described with reference to drawings.

First Embodiment

Figure 1:
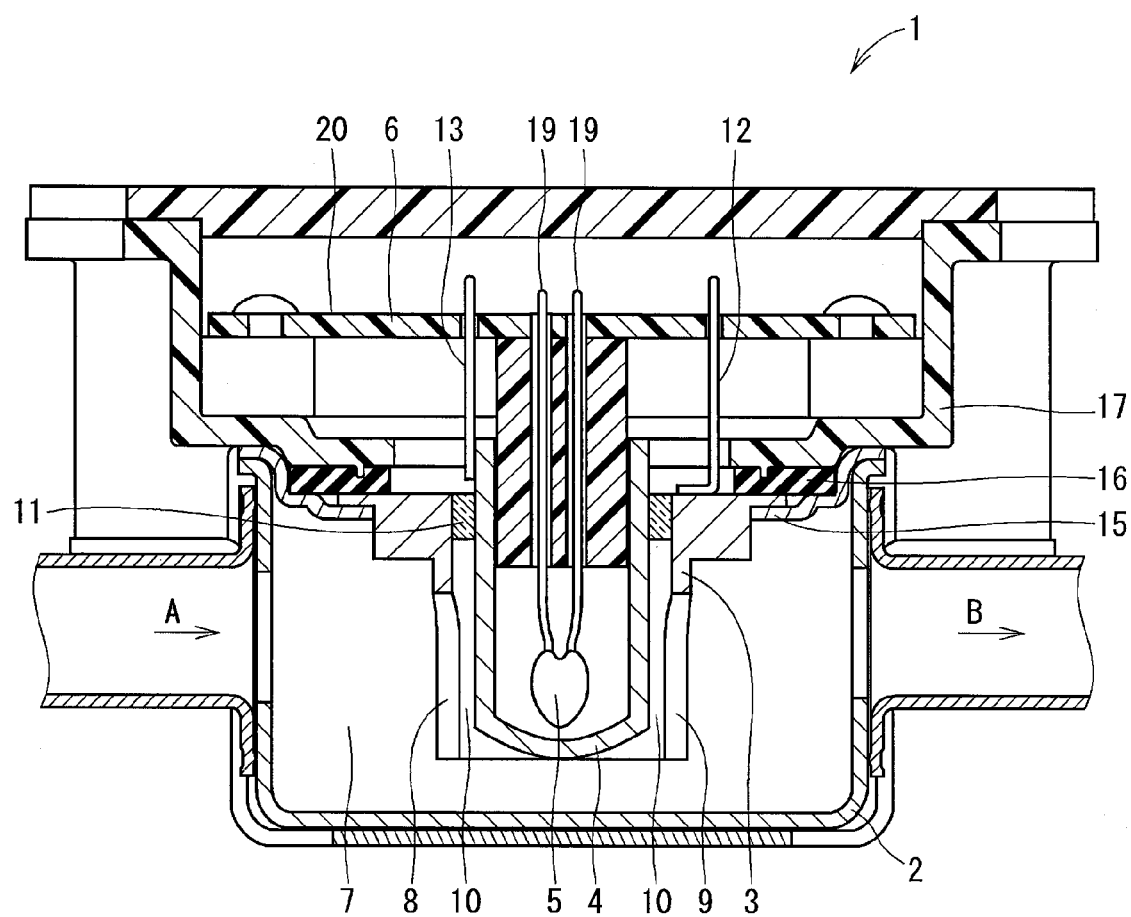
FIG. 1 is a partial sectional view showing a fuel property sensor according to a first embodiment of the present disclosure.

FIG. 1 to FIG. 7 show a first embodiment of the present disclosure. A fuel property sensor 1 of the present embodiment is equipped in a fueling system, which connects a fuel tank with a fuel injection device of a vehicle. The fuel property sensor 1 detects a concentration of ethanol, which is contained in fuel. As shown in FIG. 1, the fuel property sensor 1 includes a housing 2, an external electrode 3, an internal electrode 4, a thermistor 5, a circuit board 6, and/or the like.

The thermistor 5 functions as a temperature sensor. The housing 2 is formed of a metallic material, such as stainless steel, to be in a bottomed tubular shape. The housing 2 defines a fuel passage 7 therein. Fuel flows through the fuel passage 7 in a direction shown by arrows A and B in FIG. 1.

The external electrode 3 is formed of a metallic material, such as stainless steel, to be in a tubular shape. The external electrode 3 is equipped in the fuel passage 7 of the housing 2. The external electrode 3 has a first communication hole 8 and a second communication hole 9. The first communication hole 8 is communicated with the second communication hole 9 in a radial direction. The first communication hole 8 and the second communication hole 9 are in a U-shape and opened on a bottom side of the housing 2. The internal electrode 4 is formed of a metallic material, such as stainless steel, to be in a bottomed tubular shape. The internal electrode 4 is equipped on a radially inside of the external electrode 30. The internal electrode 4 is substantially coaxial with the external electrode 3. The internal electrode 4 and the external electrode 3 define a passage 10 therebetween through which fuel flows.

An insulative material 11 is equipped between the external electrode 3 and the internal electrode 4. The insulative material 11 fixes the internal electrode 4 with the external electrode 3. The insulative material 11 further electrically insulates the internal electrode 4 from the external electrode 3. The external electrode 3 is grounded via a terminal 12 extending through a circuit board 6. The internal electrode 4 is grounded via a terminal 13 extending through the circuit board 6. In the present configuration, the external electrode 3 and the internal electrode 4 form a capacitor by using, as a dielectric medium, fuel, which flows through the passage 10. The capacitor may be equivalent to an electrode unit. In the present embodiment, the internal electrode 4 may be one example of a first electrode, and the external electrode 3 may be one example of a second electrode.

The thermistor 5 is equipped inside the internal electrode 4. The thermistor 5 changes its electrical resistance with change in temperature, which is caused by heat transfer of fuel flowing through the passage 10. A temperature of fuel, which flows through the passage 10, is detectable according to an output signal of the thermistor 5. A lid member 15 covers the housing 2. A circuit case 17 is equipped on the lid member 15. The circuit case 17 and the lid member 15 interpose an annular elastic member 16 therebetween. A circuit board 6 is equipped inside the circuit case 17. The circuit board 6 is connected with a terminal 12 and a terminal 13. The terminal 12 is connected to the external electrode 3. The terminal 13 is connected to the internal electrode 4. The circuit board 6 is further connected with a terminal 19 of the thermistor 5.

A detection circuit 20 is formed on the circuit board 6. The detection circuit 20 repeatedly charges electricity in the capacitor formed between the external electrode 3 and the internal electrode 4 and repeatedly discharges the electricity from the capacitor. In this way, the detection circuit 20 detects a capacitance of fuel, which flows through the passage 10. The detection circuit 20 is configured to detect disconnection of the terminal 12 of the external electrode 3.

Figure 2:
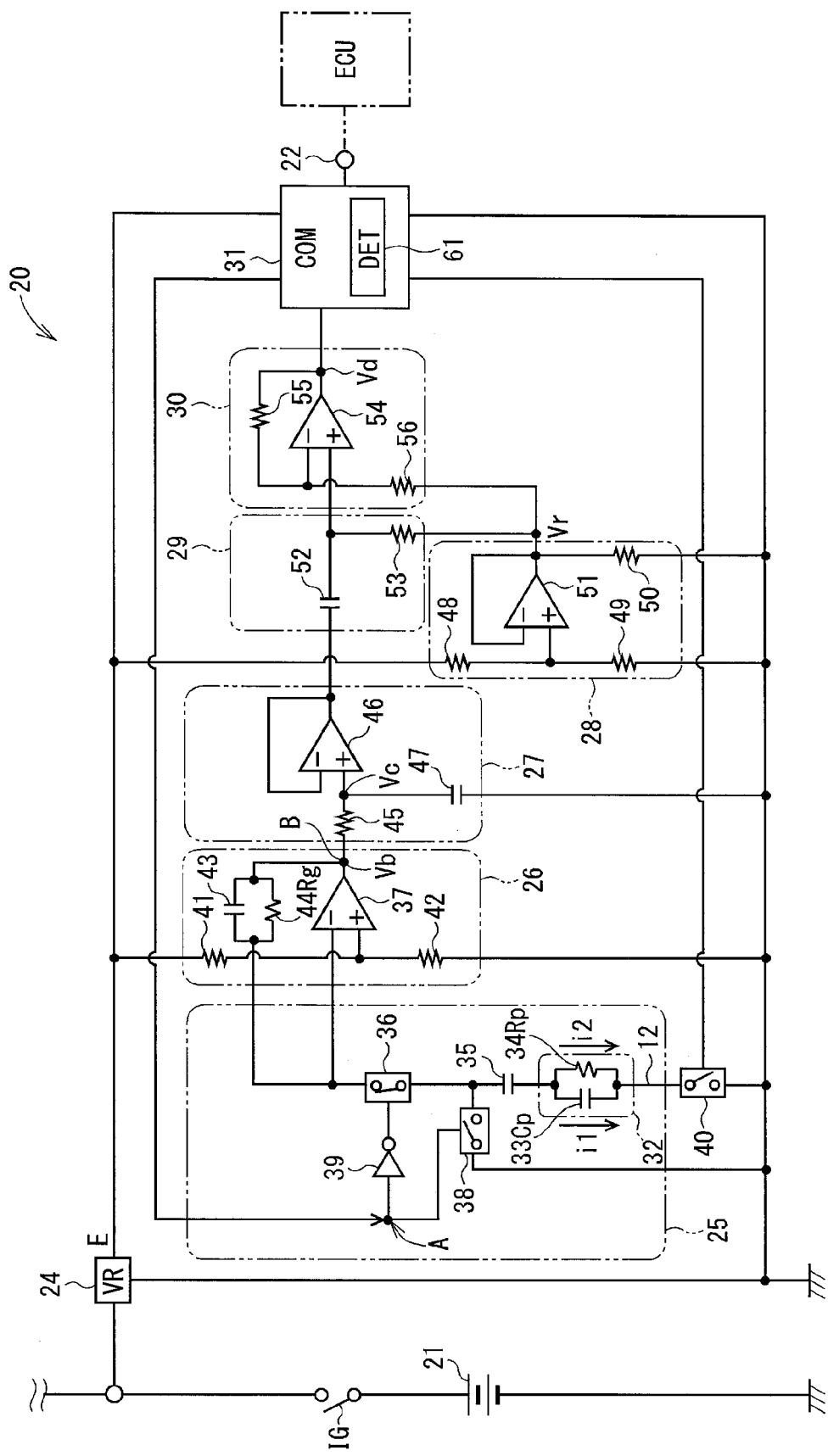
FIG. 2 is a circuit diagram showing the fuel property sensor according to the first embodiment of the present disclosure.

FIG. 2 shows an outline of the detection circuit 20 of the fuel property sensor 1. The detection circuit 20 is energized by electricity, which is supplied from a battery 21 of the vehicle though an ignition switch device IG. An output terminal 22 of the detection circuit 20 is connected to an electronic control unit (ECU). The ECU controls parameters of the engine, such as an air/fuel ratio, a fuel injection quantity, an ignition timing, and/or the like, according to a signal, which is sent from the output terminal 22 and related to the ethanol concentration. A constant-voltage regulator 24 converts a voltage of the battery 21 into a power supply voltage, which is suitable for an operation of the detection circuit 20. The present configuration applies a stabilized voltage at, for example, 5V, on the detection circuit 20 of the fuel property sensor 1.

The fuel property sensor 1 includes a switched capacitor circuit 25, an arithmetic circuit 26, a smoothing circuit 27, a reference voltage generation circuit 28, an AC coupling circuit 29, an amplification circuit 30, a microcomputer 31, and/or the like. The microcomputer 31 of the present embodiment is configured to function as a malfunction detection unit.

The switched capacitor circuit 25 includes an electrode unit 32. The electrode unit 32 is formed with the external electrode 3, the internal electrode 4, and fuel between the external electrode 3 and the internal electrode 4. In FIG. 2, the electrode unit 32 is represented with a capacitor 33 and a resistor element 34. The capacitor 33 of the electrode unit 32 has a leakage resistance related to a quantity of moisture contained in fuel and/or the like. The leakage resistance may be deemed to be equivalent to an electrical resistance, which is connected in parallel with the capacitor 33. Therefore, in FIG. 2, the electrode unit 32 is represented with the capacitor 33 (33Cp) and the leakage resistance (resistor) 34 (34Rp), which are connected in parallel with each other. The internal electrode 4 of the capacitor 33 is connected with an inverting input terminal of a first operational amplifier 37 through a coupling capacitor 35 and a first switch device 36. The internal electrode 4 of the capacitor 33 is grounded through the second switch device 38. The external electrode 3 of the capacitor 33 is grounded through the terminal 12 and the third switch device 40. The third switch device 40 of the present embodiment may be one example of a switch device.

The switched capacitor circuit 25 further includes a NOT circuit 39, a first switch device 36, and a second switch device 38. The microcomputer 31 applies two kinds of pulse waves, which are different in frequency, on an A point of the switched capacitor circuit 25. One of the pulse waves, which is at one frequency, is a first frequency pulse wave, and the other of the pulse waves, which is at the other frequency, is a second frequency pulse wave.

The first switch device 36 and the second switch device 38 are turned ON (activated) when the voltage of the pulse wave applied from the microcomputer 31 is at a high level. The first switch device 36 and the second switch device 38 are turned OFF (de-activated) when the voltage of the pulse wave is at a low level. The pulse wave is applied from the microcomputer 31 on the first switch device 36 through the NOT circuit 39. The pulse wave is applied from the microcomputer 31 directly on the second switch device 38. Therefore, the pulse wave applied on the first switch device 36 is opposite in phase from the pulse wave applied on the second switch device 38. Specifically, when the voltage of the pulse wave applied on the first switch device 36 is at the high level, the voltage of the pulse wave applied on the second switch device 38 is at the low level. Alternatively, when the voltage of the pulse wave applied on the first switch device 36 is at the low level, the voltage of the pulse wave applied on the second switch device 38 is at the high level. In the present configuration, the second switch device 38 is turned ON when the first switch device 36 is turned OFF, and the second switch device 38 is turned OFF when the first switch device 36 is turned ON.

The above-described operations of the first switch device 36 and the second switch device 38 are constant in both cases when the pulse wave sent from the microcomputer 31 is the second frequency pulse wave and when the pulse wave sent from the microcomputer 31 is the first frequency pulse wave. That is, when the microcomputer 31 applies the first frequency pulse wave on the A point of FIG. 2, the first switch device 36 and the second switch device 38 implement ON/OFF operations at the first frequency. When the microcomputer 31 applies the second frequency pulse wave on the A point of FIG. 2, the first switch device 36 and the second switch device 38 implement ON/OFF operations at the second frequency.

The noninverting input terminal of the first operational amplifier 37 of the arithmetic circuit 26 is applied with a bias voltage. The bias voltage is generated by dividing a power supply voltage at a ratio between resistor elements 41 and 42. The inverting input terminal of the first operational amplifier 37 is connected through the first switch device 36 and the coupling capacitor 35 to the positive pole terminal of the capacitor 33 (internal electrode 4). A capacitor 43 and a gain resistor element 44 are connected in parallel between the output terminal of the first operational amplifier 37 and the inverting input terminal of the first operational amplifier 37.

The output terminal of the first operational amplifier 37 is connected through a resistor element 45 of a smoothing circuit 27 to the noninverting input terminal of the second operational amplifier 46. The noninverting input terminal of the second operational amplifier 46 is grounded through the capacitor 47. In the present configuration, an output voltage Vb of the first operational amplifier 37 is applied as a smoothed output voltage Vc on the noninverting input terminal of the second operational amplifier 46. The output terminal of the second operational amplifier 46 is in common connection with the inverting input terminal of the second operational amplifier 46. The output of the second operational amplifier 46 is connected to the input of the AC coupling circuit 29.

The reference voltage generation circuit 28 is configured to generate a reference voltage Vr. The reference voltage generation circuit 28 includes resistor elements 48, 49, 50 and a third operational amplifier 51. The two resistor elements 48 and 49 are successively connected between the electric power source and the ground to divide power supply voltage and to generate the reference voltage Vr. The noninverting input terminal of the third operational amplifier 51 is connected to a connection point between the two resistor elements 48 and 49. The inverting input terminal of the third operational amplifier 51 is in common connection with the output terminal of the third operational amplifier 51. The output terminal of the third operational amplifier 51 is grounded through the resistor element 50. In the present configuration, the third operational amplifier 51 functions as a buffer to apply the reference voltage Vr.

The AC coupling circuit 29 includes a coupling capacitor 52 and a resistor element 53 to form an AC combination. The output terminal of the second operational amplifier 46 is connected to the noninverting input terminal of the fourth operational amplifier 54 through the capacitor 52. A connection point between the capacitor 52 and the noninverting input terminal of the fourth operational amplifier 54 is connected to the output terminal of the third operational amplifier 51 through the resistor element 53.

The amplification circuit 30 includes the fourth operational amplifier 54 and the resistor elements 55 and 56. The output terminal of the fourth operational amplifier 54 is connected to the inverting input terminal of the fourth operational amplifier 54 through the resistor element 55. The output terminal of the third operational amplifier 51 is connected to the inverting input terminal of the fourth operational amplifier 54 through the resistor element 56. With the present configuration, the amplification circuit 30 amplifies the voltage Vc relative to the reference voltage Vr and applies the voltage Vd on the microcomputer 31.

The microcomputer 31 is activated by application of a voltage from the constant-voltage regulator 24. The microcomputer 31 is applied with the output voltage Vd of the fourth operational amplifier 54 of the amplification circuit 30. The microcomputer 31 detects a capacitance of fuel in the electrode unit 32 according to the output voltage Vd of the fourth operational amplifier 54 and computes an ethanol concentration from the capacitance of fuel. Thus, the microcomputer 31 sends the computed ethanol concentration as an electric signal to the ECU through the output terminal 22.

Subsequently, an operation of fundamental components of the fuel property sensor 1 will be described. When the fuel property sensor 1 starts its operation, the microcomputer 31 applies the first frequency pulse wave and the second frequency pulse wave alternately on the A point in FIG. 2. Herein, ON/OFF operations of the first switch device 36 and the second switch device 38 on reception of the pulse wave at the frequency f will be first described. Subsequently, the first frequency pulse wave and the second frequency pulse wave will be described.

When the pulse wave is at the low level, the first switch device 36 is turned ON (activated), and the second switch device 38 is turned OFF (de-activated). In this case, the first operational amplifier 37 operates so that the electric potential of the noninverting input terminal becomes the same as the electric potential of the inverting input terminal. Consequently, the power supply voltage causes an electric current through the gain resistor element 44. Thus, an electric current i1 occurs through the capacitor 33, and an electric current i2 occurs through the leakage resistance 34. At this time, as shown by the time periods T1 and T3 in FIG. 3, the electric current i1 occurring through the capacitor 33 rises first, and subsequently, the electric current i1 becomes 0 when the capacitor 33 is charged. To the contrary, the electric current i2 occurring through the leakage resistance 34 is at a certain value. Strictly, the electric current (i1+i2) becomes constant, and therefore, rise of the electric current i2 is delayed. Thus, the electric currents i1 and i2 do not rise simultaneously. Nevertheless, it is noted that, the electric current i2 is described as being at the certain value for convenience. When the pulse wave is at the high level, the first switch device 36 is turned OFF (de-activated), and the second switch device 38 is turned ON (activated). In this case, the positive side of the capacitor 33 is grounded, and therefore, the charged capacitor 33 discharges its electricity. Therefore, the electric current i1 occurs through the capacitor 33 in the opposite direction from the direction in the case where the pulse wave is at the low level. At this time, as shown by the time periods T2 and T4 in FIG. 3, the electric current i1 occurring through the capacitor 33 falls first, and subsequently, the electric current i1 becomes 0 when the capacitor 33 completes its discharge. To the contrary, the electric current i2 occurring through the leakage resistance 34 becomes 0.

Figure 3:
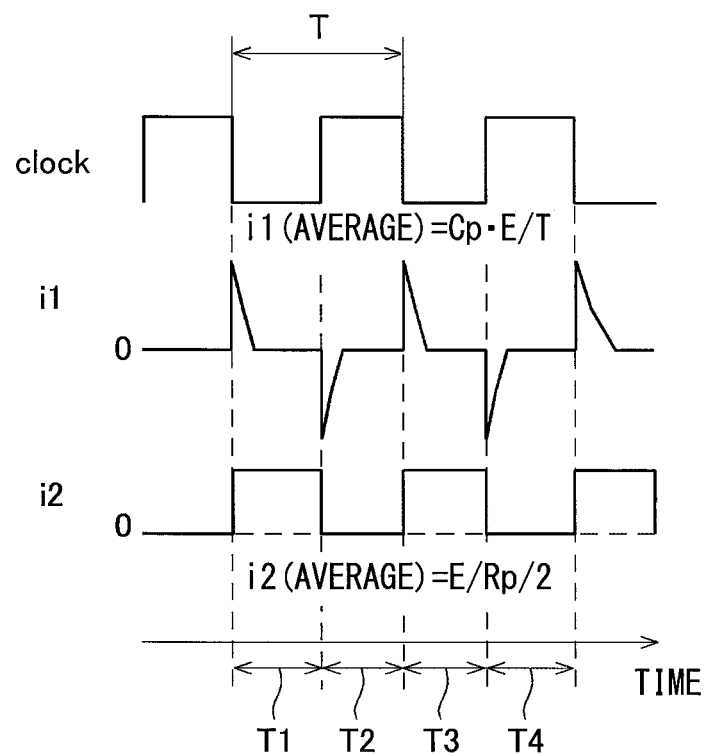
FIG. 3 is a waveform chart showing electric currents occurring in an electrode and a leakage resistance, respectively.

Subsequently, the output voltage of the first operational amplifier 37, when the first switch device and the second switch device are switched by the pulse wave at the frequency f in this way, will be described. As shown in FIG. 3, an average value of the electric current i2 is represented by the subsequent formula 1. In the formula 1, Rp represents the resistance of the leakage resistance 34, and E represents the reference voltage.

$$i2 = 0.5 \times E/Rp \qquad \text{(formula 1)}$$

An electric charge LQ accumulated in the capacitor 33 is represented by the subsequent formula 2 in which Cp represents the capacitance of the capacitor 33.

$$\Delta Q = Cp \times E \quad \text{(formula 2)}$$

An average value of the electric current i1 is a temporal differentiation of the electric charge ΔQ, and therefore, this average value is represented by the subsequent formula 3 according to the formula 2. In the formula 3, T represents a cycle and is a reciprocal number of the frequency f. That is, T is (1/f).

$$i1 = \Delta Q/T = Cp \times E/T = Cp \times T \times f \quad \text{(formula 3)}$$

It is obvious from the formula 3, a quantity of the electric current i1 discharged from the capacitor 33 is in proportion to the frequency f of the pulse wave applied on the A point of the switched capacitor circuit 25.

The voltage Vb at the B point is represented by the following formula 4 according to the formula 1 and the formula 3. In the formula 4, Rg represents a resistance of the resistor element 44.

$$Vb = E + Rg \times (i1 + i2) \quad \text{(formula 4)}$$
$$= E + Rg \times \{(Cp \times E/T) + 0.5 \times E/Rp\}$$
$$= E \times \{1 + (0.5 \times Rg/Rp) + Rg \times Cp \times f\}$$

The formula 4 represents the voltage Vb at the B point, which is an output signal from the electrode unit 32. The formula 4 includes Rp, which is the resistance of the leakage resistance 34. The resistance Rp of the leakage resistance 34 changes correspondingly to a rate of conductive impurities, which is contained in fuel, to impair a measurement accuracy of ethanol concentration.

In consideration of this, the fuel property sensor 1 according to the first embodiment of the present disclosure causes the microcomputer 31 to switch between the first frequency pulse wave and the second frequency pulse wave alternately. Thus, the microcomputer 31 switches the frequency of the ON/OFF operation of the first switch device 36 and the second switch device 38 between the frequency f1 and the frequency f2 alternately. In this way, the fuel property sensor 1 obtains two kinds of the voltages Vb at the B point correspondingly to the frequencies f1 and f2.

The subsequent formula 5 represents the $Vb_{f1}$, which is the voltage at the B point when the first switch device 36 and the second switch device 38 implement the ON/OFF operations at the frequency f1 during the fuel property sensor 1 is in operation.

$$Vb_{f1} = E \times \{1 + (0.5 \times Rg/Rp) + Rg \times Cp \times f1\} \quad \text{(formula 5)}$$

The subsequent formula 6 represents the $Vb_{f2}$, which is the voltage at the B point when the first switch device 36 and the second switch device 38 implement the ON/OFF operations at the frequency f2.

$$Vb_{f2} = E \times \{1 + (0.5 \times Rg/Rp) + Rg \times Cp \times f2\} \quad \text{(formula 6)}$$

The subsequent formula 7 is obtained by subtracting $V_{f2}$ from $V_{f1}$.

$$Vb_{f1} - Vb_{f2} = E \times (f1 - f2) \times Rg \times Cp \quad \text{(formula 7)}$$

It is obvious from the formula 7 that the resistance Rp of the leakage resistance 34 is eliminated from the formula, which indicates the output signal related to the voltage Vb at the B point, that is, which is related to the ethanol concentration. In this way, the present configuration reduces a factor, which relates to decrease in a detection accuracy of the ethanol concentration of the fuel property sensor 1.

The electrode unit 32 detects, as the ethanol concentration, the voltage Vb at the B point. The signal at the voltage Vb is transmitted through the smoothing circuit 27 and the AC coupling circuit 29 and is amplified by the amplification circuit 30 to an appropriate voltage at which the microcomputer 31 is enabled to process the amplified signal. Thus, the microcomputer 31 receives the amplified signal.

Figure 7:
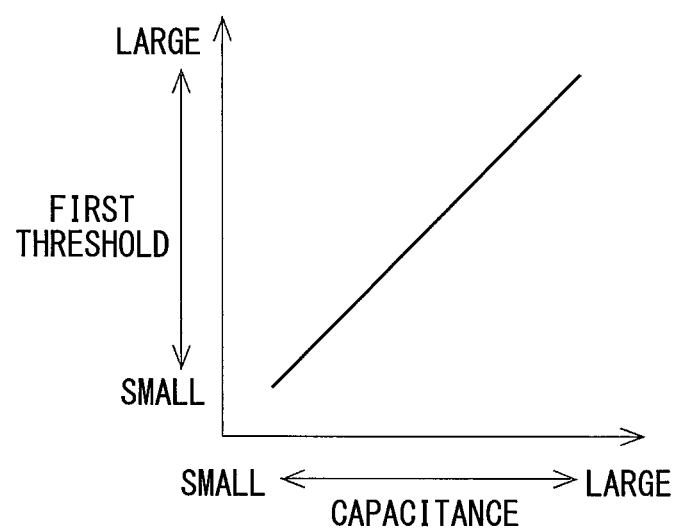
FIG. 7 is a graph showing a relation between the capacitance and a first threshold.

Subsequently, a malfunction detection processing of the fuel property sensor 1 will be described with reference to FIG. 4, FIG. 5, and FIG. 7. The malfunction detection processing detects disconnection of the external electrode 3 according to a capacitance, which is detected by switching ON (close) and OFF (open) the third switch device 40. The third switch device 40 is equipped in the detection circuit 20.

In general, the housing 2 of the fuel property sensor 1 is electrically connected to a ground of the battery 21 through a metallic component of the fueling system of the vehicle. Therefore, when the external electrode 3 causes disconnection, the fuel property sensor 1 forms a capacitor between the housing 2 and the external electrode 3, in addition to the capacitor 33 formed between the internal electrode 4 and the external electrode 3. In this case, when electric power is supplied to the internal electrode 4, the two capacitors are electrically connected in series. Therefore, in this case, the detection circuit 20 sends a capacitance, which is different from the capacitance in a normal state. In addition, an electric potential of the metallic component, which is connected with the housing 2, may generally receive noise from various electric components equipped to the vehicle. Therefore, electric potential of the metallic component is generally unstable. Thus, the capacitance, which is sent from the detection circuit 20, may become unstable when the terminal 12 of the external electrode 3 causes disconnection.

Figure 4:
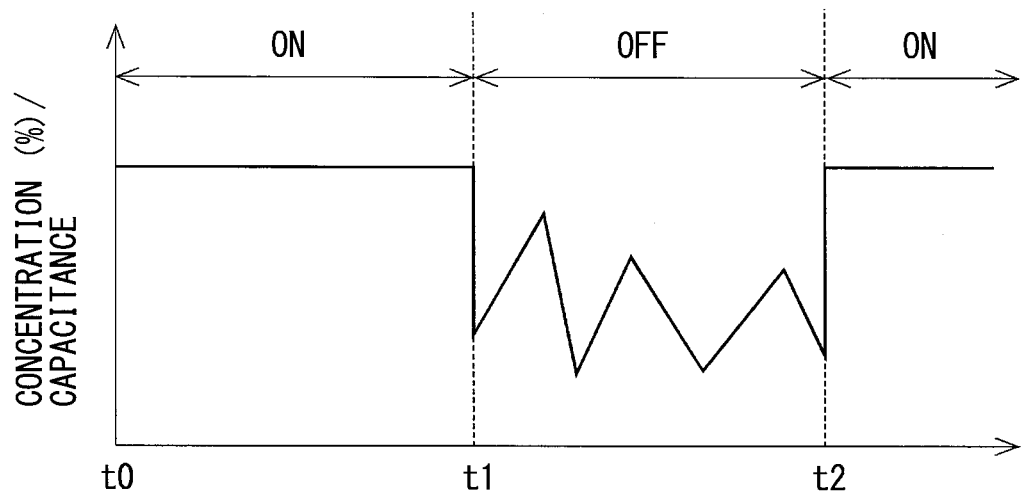
FIG. 4 is a time chart showing a capacitance detected when a switch device is turned ON and OFF in a normal state.

FIG. 4 shows data of the capacitance, which is detected by switching ON and OFF the third switch device 40, in the state where the terminal 12 of the external electrode 3 does not cause disconnection. In FIG. 4, the third switch device 40 is turned ON from the time t0 to the time t1, the third switch device 40 is turned OFF from the time t1 to the time t2, and the third switch device 40 is turned ON after the time t2. The capacitance sent when the third switch device 40 is turned OFF becomes unstable and small compared with the capacitance sent when the third switch device 40 is turned ON. It is considered that this phenomenon occurs due to occurrence of a capacitive coupling and noise of various electrical components equipped to the vehicle.

Figure 5:
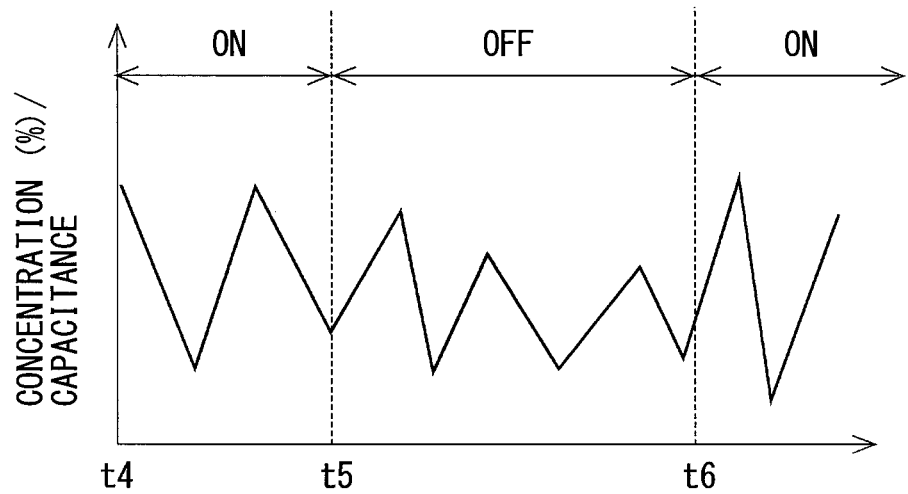
FIG. 5 is a time chart showing a capacitance detected when the switch device is turned ON and OFF in a disconnection state.

FIG. 5 shows data of the capacitance, which is detected by switching ON and OFF the third switch device 40, in the state where the terminal 12 of the external electrode 3 causes disconnection. In FIG. 5, the third switch device 40 is turned ON from the time t4 to the time t5, the third switch device 40 is turned OFF from the time t5 to the time t6, and the third switch device 40 is turned ON after the time t6. Both the capacitances sent when the third switch device 40 is turned OFF and the capacitance sent when the third switch device 40 is turned ON are continually unstable.

The fuel property sensor 1 is configured to simulate disconnection of the terminal 12 of the external electrode 3 by turning OFF the third switch device 40. Therefore, the malfunction detection unit 61 is configured to detect disconnection of the external electrode 3 by comparing the capacitance, which is detected by the detection circuit 20 when the third switch device 40 is turned ON, and the capacitance, which is detected by the detection circuit 20 when the third switch device 40 is turned OFF. Specifically, the malfunction detection unit 61 detects disconnection of the external electrode 3 by comparing a difference, which is between the capacitance when the third switch device 40 is turned ON and the capacitance when the third switch device 40 is turned OFF, with a first threshold stored in the microcomputer 31. The value of the first threshold is determined according to an experimental result and/or the like.

As the ethanol concentration becomes lower to reduce the capacitance of the electrode unit 32, the difference between the capacitances detected by turning ON and OFF the third switch device 40 becomes smaller. In consideration of this, with reference to the data map shown in FIG. 7, the microcomputer 31 sets the first threshold smaller, as the capacitance detected when turning the third switch device 40 ON and OFF becomes smaller. In this way, the malfunction detection unit 61 is enabled to detect disconnection of the external electrode 3 correctly.

Furthermore, the malfunction detection unit 61 is configured to detect disconnection of the external electrode 3 according to one of the subsequent detection results (1) to (3) and/or a combination of the subsequent detection results (1) to (3).

(1) The malfunction detection unit 61 detects disconnection of the wiring, which connects the second electrode with the ground, when a difference, which is between the capacitance detected when the third switch device 40 is turned ON at a predetermined time and the capacitance detected when the third switch device 40 is turned ON after elapse of a specific time period subsequent to the turning ON, is greater than a second threshold. With the present method, the malfunction detection unit 61 is enabled to detect instability (variation) of the capacitance sent from the detection circuit 20. The malfunction detection unit 61 detects disconnection of the second electrode when the capacitance sent from the detection circuit 20 is unstable. The second threshold is beforehand set at a value greater than a variation in the capacitance, which is detected when the second electrode does not cause disconnection, according to an experimental result and/or the like.

(2) The malfunction detection unit 61 detects disconnection of the wiring, which connects the second electrode with the ground, when a difference, which is between an average value of the capacitances detected for multiple times when the third switch device 40 is turned ON and an average value of the capacitances detected for multiple times when the third switch device 40 is turned OFF, is less than a first threshold. The present configuration enables to enhance certainty of detection of a malfunction.

(3) The malfunction detection unit 61 detects disconnection of the wiring, which connects the second electrode with the ground, when a difference, which is between an integration value of the capacitance detected when the third switch device 40 is turned ON for a specific time period and an integration value of the capacitance detected with the detection circuit 20 when the third switch device 40 is turned OFF for a specific time period, is less than a third threshold. The value of the third threshold is determined according to an experimental result and/or the like. When the external electrode 3 causes disconnection, the capacitance sent from the detection circuit 20 becomes surely less than the capacitance before the disconnection even though being instable. In consideration of this, disconnection of the wiring, which connects the second electrode with the ground, can be detected according to the integration value of the capacitance when the third switch device 40 is turned ON for the specific time period and the integration value of the capacitance when the third switch device 40 is turned OFF for the specific time period. The microcomputer 31 sets the value of the third threshold smaller as the difference, which is between the integration value of the capacitance detected when the third switch device 40 is turned ON and the integration value of the capacitance detected when the third switch device 40 is turned OFF, becomes small. In this way, the malfunction detection unit 61 is enabled to detect disconnection of the external electrode 3 correctly.

According to the present embodiment, the malfunction detection unit 61 of the microcomputer 31 implements the malfunction detection processing. It is noted that, according to a modification of the present embodiment, a microcomputer, which is to implement the malfunction detection processing, may be provided separately from the microcomputer 31, and/or the ECU of the vehicle may be configured to implement the malfunction detection processing.

Figure 6:
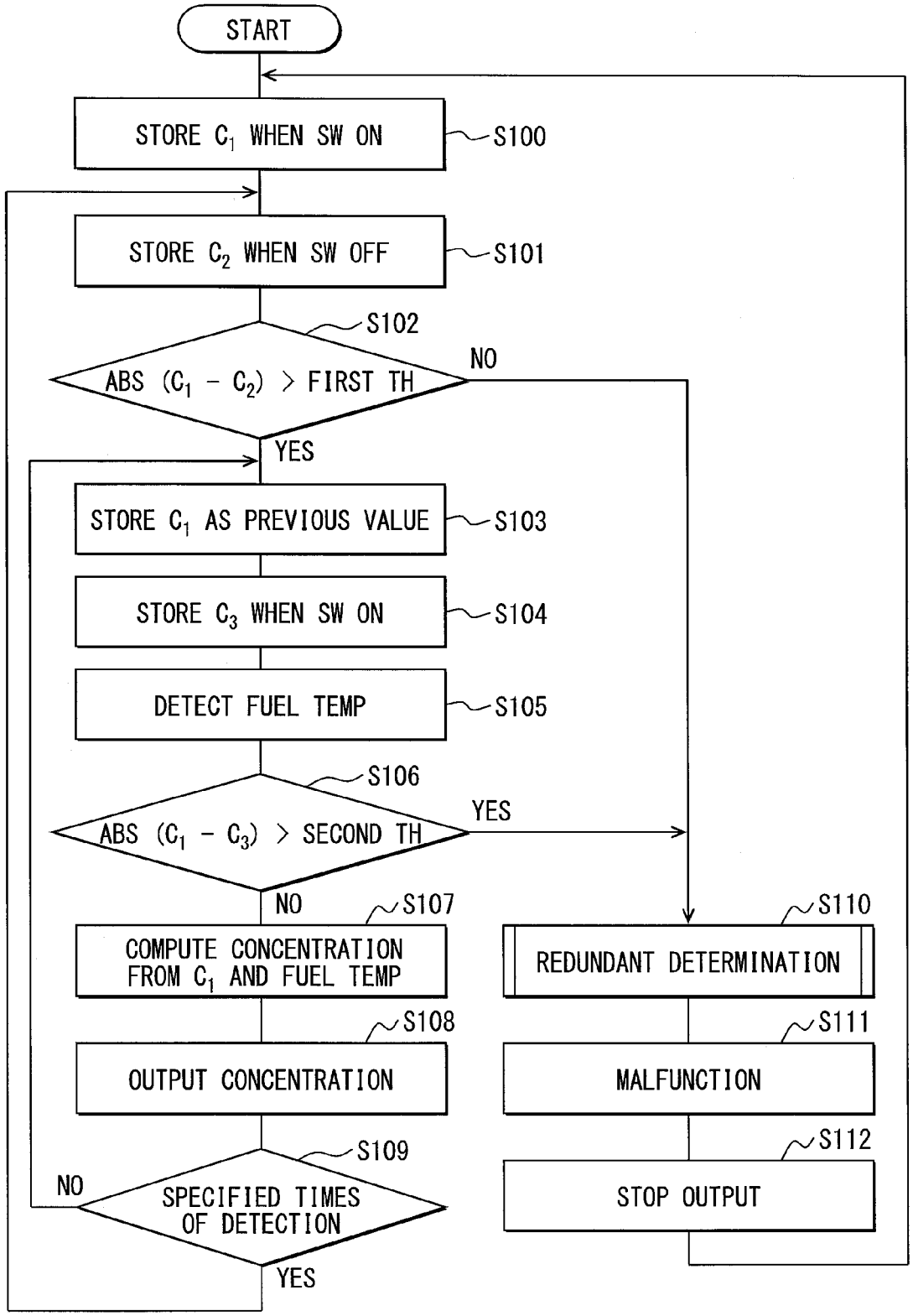
FIG. 6 is a flowchart showing a malfunction detection processing according to the first embodiment of the present disclosure.

Subsequently, the malfunction detection processing implemented by the fuel property sensor 1 will be described with reference to the flowchart of FIG. 6. When the ignition IG of the engine is turned ON, at step S100, the detection circuit 20 of the fuel property sensor 1 first detects the capacitance $C_1$ in the state where the third switch device 40 is turned ON. The capacitance $C_1$ is stored in the memory of the microcomputer 31. Subsequently, at step S101, the detection circuit 20 detects the capacitance $C_2$ in the state where the third switch device 40 is turned OFF. The capacitance $C_2$ is stored in the memory of the microcomputer 31 (S101).

Subsequently, at step S102, the malfunction detection unit 61 determines whether an absolute value of the difference, which is between the capacitance $C_1$ detected at step S100 and the capacitance $C_2$ detected when the third switch device 40 is turned OFF, is greater than the first threshold beforehand stored in the microcomputer 31. When step S102 makes a positive determination, the processing proceeds to step S103. To the contrary, when step S102 makes a negative determination, the difference, which is between the capacitance detected by turning ON and OFF the third switch device 40, is less than the first threshold. Therefore, it is determined that the external electrode 3 may cause disconnection. In this case, the processing proceeds to step S110. In the present embodiment, steps S100, S101, and S102 may be examples of a first step, a second step, and a third step, respectively.

At step S103, the capacitance $C_1$ detected at step S100 is stored as a previous value in the memory of the microcomputer 31. Subsequently, at step S104, the detection circuit 20 detects the capacitance $C_3$ in the state where the third switch device 40 is turned ON. The capacitance $C_3$ is stored in the memory of the microcomputer 31.

Subsequently, at step S105, the microcomputer 31 detects a temperature of fuel, which flows through the passage 10, according to an output signal of the thermistor 5. The temperature of fuel is used for detection of the ethanol concentration in a normal state.

Subsequently, at step S106, the malfunction detection unit 61 determines whether an absolute value of the difference, which is between the capacitance $C_1$ detected as the previous value at step S103 and the capacitance $C_3$ detected at step S104, is greater than the second threshold beforehand stored in the microcomputer 31. When step S106 makes a negative determination, the processing proceeds to step S107 on determination that the external electrode 3 does not cause disconnection. To the contrary, when step S106 makes a positive determination, a variation in the capacitance, which is detected by turning ON the third switch device 40, is greater than the second threshold. Therefore, it is determined that the external electrode 3 may cause disconnection. In this case, the processing proceeds to step S110.

At step S107, the ethanol concentration is computed from the capacitance $C_1$ detected at step S100 and the temperature of fuel detected at step S105. At step S108, the microcomputer 31 sends the ethanol concentration to the ECU. At step S109, the number of times, by which the processing of step S108 has been implemented, is counted. When the number of times is less than a specified number of times, the processing proceeds to step S103, and the processing subsequent to step S103 is implemented. Alternatively, at step S109, when the number of times, by which the processing at step S108 has been implemented, becomes greater than or equal to the specified number of times, the processing proceeds to step S101. Thus, the processing subsequent to step S101 is implemented. In this way, the present configuration enables to determine whether the external electrode 3 causes disconnection for every specified number of times.

Subsequently, the processing at step S110, which is proceeded with on determination that the external electrode 3 may cause disconnection, will be described. The processing at step S110 is proceeded with on negative determination at step S102 or on positive determination at step S106. At step S110, the microcomputer 31 enhances certainty of the disconnection detection processing with a redundant determination. Specifically, at step S110, the processing at step S100, S101, and S102 is implemented for multiple times. Alternatively, at step S110, the processing at step S103, S104, and S105 is implemented for multiple times. At step S110, a difference between an average value of the capacitances, which are detected for multiple times in the state where the third switch device 40 is turned ON, and an average value of the capacitances, which are detected for multiple times in the state where the third switch device 40 is turned OFF, may be compared with the first threshold.

As a result of the redundant determination implemented at step S110, when it is determined that the state of the capacitance, which is detected when the third switch device 40 is turned ON, is deemed to be the same as the state of the capacitance, which is detected when the third switch device 40 is turned OFF, the processing proceeds to step S111. At step S111, a malfunction determination is made on determination that the external electrode 3 causes disconnection. At subsequent step S112, output of the ethanol concentration from the fuel property sensor is stopped. Subsequent to step S112, the processing proceeds to step S100. Thus, the processing subsequent to step S100 is implemented again.

The first embodiment produces the following operation effects.

(1) According to the first embodiment, the malfunction detection unit 61 detects disconnection of the external electrode 3 when the difference, which is between the capacitance when the third switch device 40 is turned ON and the capacitance when the third switch device 40 is turned OFF, is less than the first threshold. Disconnection of the external electrode 3 can be simulated by turning OFF the third switch device 40. Therefore, the fuel property sensor 1 is configured to detect the capacitance when turning ON the third switch device 40 and to detect the capacitance when turning OFF the third switch device 40. The fuel property sensor 1 is further configured to detect existence of disconnection of the external electrode 3 according to the difference between the detected capacitances.

(2) The malfunction detection unit 61 sets the first threshold at a small value when the capacitance, which is detected with the detection circuit 20 by turning ON the third switch device 40 and/or turning OFF the third switch device 40, is small. As the ethanol concentration becomes lower to reduce the capacitance of the electrode unit 32, the difference between the capacitances detected by turning ON and OFF the third switch device 40 becomes smaller. Therefore, the malfunction detection unit 61 is enabled to detect disconnection of the external electrode 3 correctly by changing the first threshold according to the capacitance, which is detected with the detection circuit 20.

(3) The malfunction detection unit 61 detects disconnection of the external electrode 3, when a difference, which is between the capacitance detected when the third switch device 40 is turned ON at a predetermined time and the capacitance detected when the third switch device 40 is turned ON at another predetermined time after elapse of a specific time period subsequent to the predetermined time (turning ON), is greater than the second threshold. In this way, the malfunction detection unit 61 is configured to detect disconnection of the external electrode 3 according to a variation in the capacitance detected in the state where the switch is turned ON at a specific predetermined time interval. Therefore, the fuel property sensor is enabled to enhance certainty of the disconnection detection processing.

(4) The malfunction detection unit 61 detects disconnection of the external electrode 3, when the difference, which is between the average value of the capacitances detected for multiple times when the third switch device 40 is turned ON and the average value of the capacitances detected for multiple times when the third switch device 40 is turned OFF, is less than the first threshold. The malfunction detection unit 61 is enabled to enhance certainty of the disconnection detection processing by implementing the redundant determination.

(5) The malfunction detection unit 61 detects disconnection of the external electrode 3, when the difference, which is between the integration value of the capacitance detected when the switch device is turned ON for the specific time period and the integration value of the capacitance detected when the switch device is turned OFF for the specific time period, is less than the third threshold. In this way, the malfunction detection unit 61 detects the integration value of the capacitance in the specific time period, thereby to enable to enhance certainty of the disconnection detection processing, regardless of a variation in the capacitance caused by a disturbance and/or the like.

(Modification)

According to a modification of the first embodiment, when a negative determination is made at step S102, the malfunction detection unit 61 may proceed the processing to step S110 subsequent to implementing the processing at steps S103, S104, and S106. In this way, the fuel property sensor is enabled to enhance certainty of the disconnection detection processing.

Second Embodiment

Figure 8:
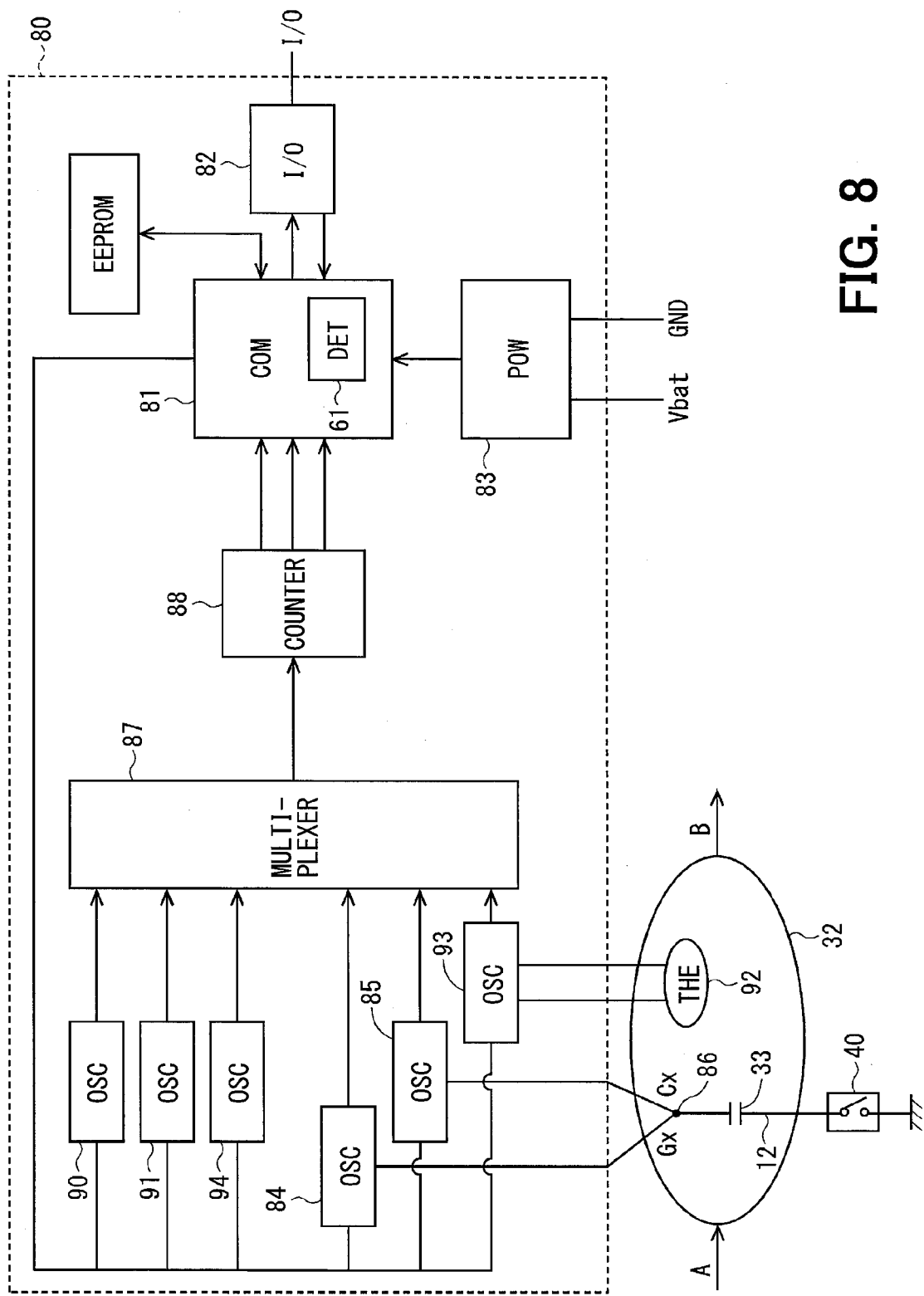
FIG. 8 is a circuit diagram showing a fuel property sensor according to a second embodiment of the present disclosure.
Figure 9:
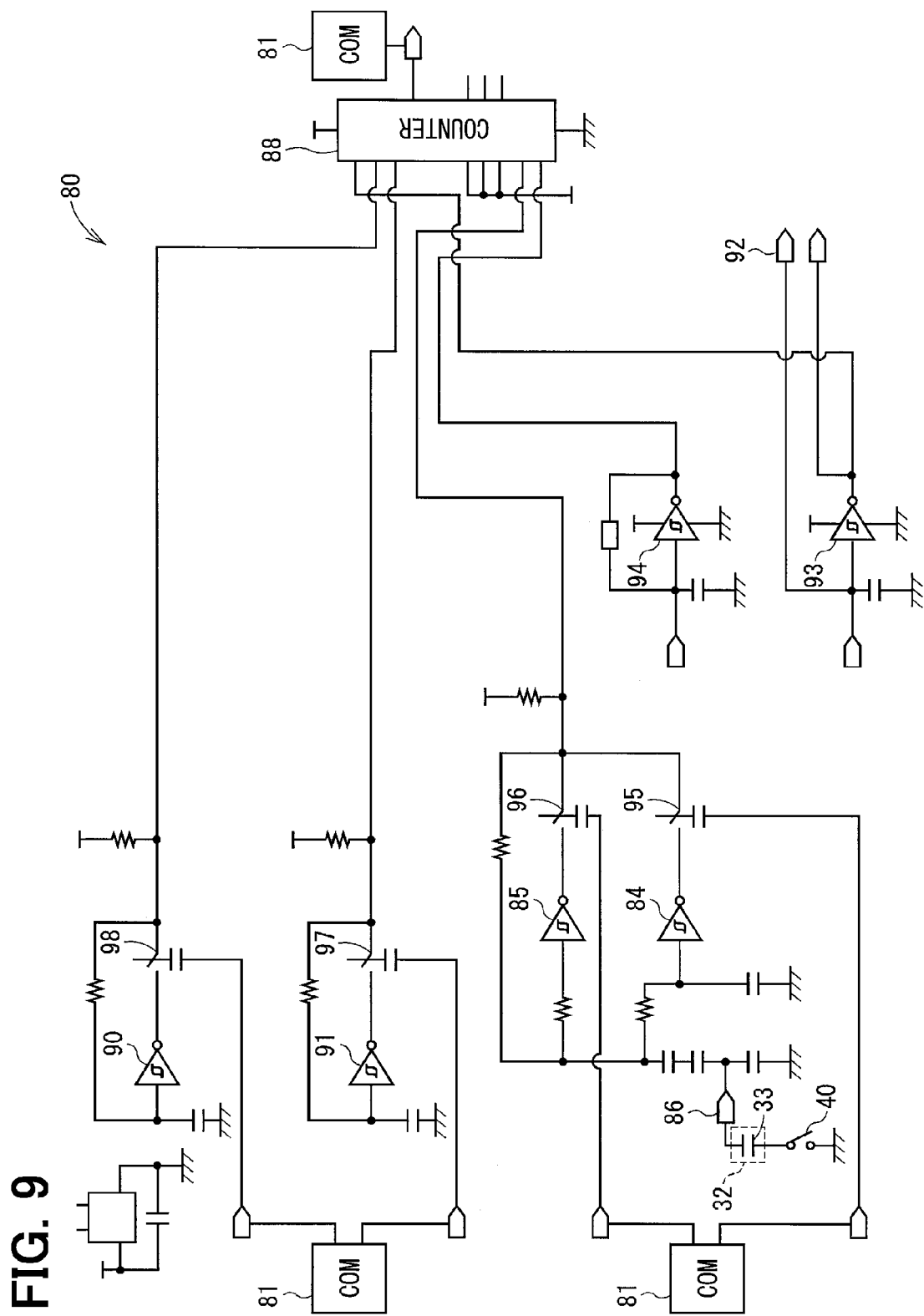
FIG. 9 is a circuit diagram showing the fuel property sensor according to the second embodiment of the present disclosure.

FIG. 8 to FIG. 9 show a second embodiment of the present disclosure. In the second embodiment, the configuration of the detection circuit 80 differs from the configuration of the circuit of the first embodiment. As shown in FIG. 8 and FIG. 9, the capacitor 33 is formed of the external electrode 3, the internal electrode 4, and fuel. The third switch device 40 is equipped between the capacitor 33 and the ground.

As shown in FIG. 8, the microcomputer 81 is programmed to acquire information, which relates to the capacitance, the temperature, and the electric conduction rate (i.e., conductance and volume), detected with the electrode unit 32. The microcomputer 81 is further programmed to compare the acquired information with data stored in the ROM of the microcomputer 81, thereby to measure a quantity of ethanol contained in fuel. The microcomputer 81 sends a signal relating to the concentration of ethanol to the ECU of the engine through the output terminal 82. The electric power source 83 supplies an electric power to the microcomputer 81.

According to the second embodiment, the electric conduction rate of fuel and the dielectric constant of fuel are detected by using the electrode unit 32. Two different oscillators 84 and 85 send signals selectively to the capacitor 33 and to implement measurement of two distinct quantities, for example, the electric conduction rates and the capacitances, separately. The detection circuit 80 includes a connection terminal 86 between the capacitor 33 and the oscillators 84 and 85. The configuration according to the second embodiment switches the output of the oscillators 84 and 85 instead of switching the connection to the capacitor 33. It is noted that, in the configuration of the second embodiment, a parasitic capacitance does not substantially exert influence on the capacitance to be measured.

The detection circuit 80 includes a multiplexer 87, which is configured to receive signals sent from the oscillators 84 and 85. According to one example, one oscillator 84 operates in a megahertz order frequency range, and the other oscillator 85 operates in a kilohertz order frequency range. These frequencies are relatively high. In consideration of this, a counter 88 is equipped between the multiplexer 87 and the microcomputer 81 to function as a divider. Thus, the microcomputer 81 is enabled to process the signals from the oscillators 84 and 85. The detection circuit 80 is configured to operate the oscillators 84 and 85 independently at different frequencies, respectively, to operate the capacitor 33 in two modes according to activation of which oscillator.

Reference oscillators 90 and 91 are equipped to compensate drift and aging caused in the detection circuit 80. One reference oscillator 90 is configured to adapt to a lower end of an expected spectrum of a quantity of alcoholic (alcoholic content) contained in fuel. The other reference oscillator 91 is configured to adapt to an opposite end (higher end) of the expected spectrum of the quantity of alcoholic contained in fuel. For example, the reference oscillator 90 may be adapted to 10% of the alcoholic content, and the other reference oscillator 91 may be adapted to 80% of the alcoholic content. It may be desirable that the reference oscillators 90 and 91 may maintain a constant value (constant performance) throughout entire life of the fuel property sensor.

Temperature of fuel mixture may be a distinct factor to be taken into consideration in detection of components contained in fuel mixture by using a capacitance and an electric conduction rate. The detection circuit 80 includes a distinct oscillator 93 connected with the thermistor 92, which is for acquiring temperature information on fuel. A reference oscillator 94 is equipped to provide calibration information to compensate drift and/or change caused in the oscillator 93 due to aging.

The microcomputer 81 is programmed to switch between one oscillator 84 and the other oscillator 85 selectively to measure the electric conduction rate and/or the capacitance. In FIG. 9, electronic switch devices 95 and 96 are equipped. The electronic switch devices 95 and 96 are selectively activated by the microcomputer 81 to activate the oscillator desirably and to measure the state desirably. The microcomputer 81 controls the electronic switch devices 97 and 98 to select one of the reference oscillators 90 and 91.

According to the second embodiment, the malfunction detection unit 61 detects disconnection of the external electrode 3 according to the capacitance, which is detected by switching ON and OFF the third switch device 40. In the fuel property sensor of the second embodiment, the malfunction detection unit 61 is configured to produce an operation effect similarly to the first embodiment.

Other Embodiments (1) According to the above-described embodiments, the internal electrode 4 is configured to be applied with a voltage, and the external electrode 3 is connected to the ground. According to another embodiment, the external electrode may be configured to be applied with a voltage, and the internal electrode may be connected to the ground. In this case, the external electrode may be one example of a first electrode, and the internal electrode may be one example of a second electrode.

(2) According to the above-described embodiments, the fuel property sensor detects the concentration of ethanol contained included in fuel from the electrical property between the electrodes. According to another embodiment, the fuel property sensor may be configured to detect another state of fuel, such as oxidization of fuel and/or deterioration of fuel, from the electrical property between electrodes.

(3) According to the embodiments, the fuel property sensor detects the capacitance between the electrodes and detects the property of fuel and the state of fuel from the dielectric constant of fuel. According to another embodiment, the fuel property sensor may detect a resistance between electrodes and may detect a property of fuel and a state of fuel from an electric conduction rate of fuel.

As described above, according to the present disclosure, the fuel property sensor for detecting a capacitance of fuel includes the malfunction detection unit and the switch device, which is equipped between the electrode unit and the ground. The malfunction detection unit is configured to detect disconnection between the electrode unit and the ground when the difference between the capacitance, which is detected when the switch device is turned ON, and the capacitance, which is detected when the switch device is turned OFF, is smaller than the first threshold. The fuel property sensor is configured to simulate disconnection of the wiring, which connects the electrode unit with the ground, by turning OFF the switch device, which is equipped between the electrode unit and the ground. The fuel property sensor sends a capacitance, which is different from the capacitance in the normal state, when the electrode unit and the ground are disconnected from each other to cause, for example, a capacitive coupling and/or the like. The fuel property sensor is configured to detect the capacitance when turning ON the switch device and to detect the capacitance when turning OFF the switch device. The fuel property sensor is further configured to detect existence of disconnection between the electrode unit and the ground according to the difference between the detected capacitances.

According to the method for detecting malfunction of the fuel property sensor, disconnection between the wiring, which connects the second electrode with the ground, is detected when the difference between the capacitance, which is detected when the switch device is turned ON, and the capacitance, which is detected when the switch device is turned OFF, is less than the first threshold. The first threshold may be changed according to the capacitance detected when the switch device is ON.

It should be appreciated that while the processes of the embodiments of the present disclosure have been described herein as including a specific sequence of steps, further alternative embodiments including various other sequences of these steps and/or additional steps not disclosed herein are intended to be within the steps of the present disclosure.

While the present disclosure has been described with reference to preferred embodiments thereof, it is to be understood that the disclosure is not limited to the preferred embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A fuel property sensor comprising:
   an electrode unit including a first electrode and a second electrode, the first electrode and the second electrode defining a space therebetween, the space configured to flow fuel therethough;
   a detection circuit connected to the first electrode and configured to charge and discharge the electrode unit to detect a capacitance of fuel, which flows through the space;
   a switch device equipped to a wiring, which connects the second electrode with a ground, the switch device configured to simulate disconnection between the second electrode and the ground; and
   a malfunction detection unit configured
      to compare a difference between a capacitance detected with the detection circuit when the switch device is turned ON and a capacitance detected with the detection circuit when the switch device is turned OFF with a first threshold and
      to detect disconnection of the wiring, which connects the second electrode with the ground, when the difference is smaller than the first threshold.

2. The fuel property sensor according to claim 1, wherein the malfunction detection unit is further configured to set the first threshold at a smaller value, as a capacitance, which is detected with the detection circuit when the switch device is turned ON or when the switch device is turned OFF, becomes smaller.

3. The fuel property sensor according to claim 1, wherein the malfunction detection unit is further configured to detect disconnection of the wiring, which connects the second electrode with the ground, when a difference between a capacitance, which is detected with the detection circuit when the switch device is turned ON at a predetermined time, and a capacitance, which is detected with the detection circuit when the switch device is turned ON at a time after an elapse of a specific time period subsequent to the predetermined time, is greater than a second threshold.

4. The fuel property sensor according to claim 1, wherein the malfunction detection unit is further configured to detect disconnection of the wiring when a difference between an average value of capacitances, which are detected with the detection circuit for a plurality of times when the switch device is turned ON, and an average value of capacitances, which are detected with the detection circuit for a plurality of times when the switch device is turned OFF, is smaller than the first threshold.

5. The fuel property sensor according to claim 1, wherein the malfunction detection unit is further configured to detect disconnection of the wiring when a difference between an integration value of a capacitance, which is detected with the detection circuit when the switch device is turned ON for a specific time period, and an integration value of a capacitance, which is detected with the detection circuit when the switch device is turned OFF for a specific time period, is smaller than a third threshold.

6. A method for detecting malfunction of the fuel property sensor according to claim 1, the method comprising:
   detecting, at a first step, the capacitance when the switch device is turned ON;
   detecting, at a second step, the capacitance when the switch device is turned OFF; and
   detecting, at a third step, disconnection of the wiring, which connects the second electrode with the ground, when a difference between the capacitance, which is detected at the first step, and the capacitance, which is detected at the second step, is less than the first threshold.

7. The method according to claim 6, the method further comprising:
   detecting, at a fourth step, the capacitance when the switch device is turned ON after an elapse of a specific time period subsequent to the first step; and
   detecting, at a fifth step, disconnection of the wiring, which connects the second electrode with the ground, when a difference between the capacitance, which is detected at the first step, and the capacitance, which is detected at the fourth step, is greater than a second threshold.

8. The fuel property sensor according to claim 1, further comprising:
   a housing electrically connected to a ground of a battery.

9. The fuel property sensor according to claim 8, further comprising:
   the battery configured to energize the detection circuit.

10. The fuel property sensor according to claim 1, wherein the malfunction detection unit is further configured to set the first threshold at a smaller value, as a capacitance, which is detected with the detection circuit when the switch device is turned ON and OFF, becomes smaller.

11. The fuel property sensor according to claim 1, wherein the switch device is configured to connect the second electrode with the ground and to disconnect the second electrode from the ground.

12. The fuel property sensor according to claim 1, further comprising:
   a first storage unit configured to store the capacitance detected with the detection circuit when the switch device is turned ON; and
   a second storage unit configured to store the capacitance detected with the detection circuit when the switch device is turned OFF.

13. A fuel property sensor comprising:
   an electrode unit including a first electrode and a second electrode, the first electrode and the second electrode defining a space therebetween, the space configured to flow fuel therethough;
   a detection circuit connected to the first electrode and configured to charge and discharge the electrode unit to detect a capacitance of fuel, which flows through the space;
   a switch device equipped to a wiring, which connects the second electrode with a ground, the switch device configured to simulate disconnection between the second electrode and the ground;
   a comparison unit configured to compare a difference between a capacitance detected with the detection circuit when the switch device is turned ON and a capacitance detected with the detection circuit when the switch device is turned OFF with a first threshold; and
   a malfunction detection unit configured
      to determine whether the difference is smaller than the first threshold and to detect disconnection of the wiring, which connects the second electrode with the ground, on determination that the difference is smaller than the first threshold.

14. The fuel property sensor according to claim 13, wherein the malfunction detection unit is further configured to set the first threshold at a smaller value, as a capacitance, which is detected with the detection circuit when the switch device is turned ON or when the switch device is turned OFF, becomes smaller.

15. The fuel property sensor according to claim 13, wherein the switch device is configured to connect the second electrode with the ground and to disconnect the second electrode from the ground.

\* \* \* \* \*